United States Patent
den Boer

(10) Patent No.: US 7,248,917 B2
(45) Date of Patent: Jul. 24, 2007

(54) SELF TREATMENT DEVICE

(75) Inventor: Willem Maurits Johannes den Boer, Rozendaal (NL)

(73) Assignee: De Smidsberg B.V. (NL)

( * ) Notice: Subject to any disclaimer, the term of this patent is extended or adjusted under 35 U.S.C. 154(b) by 521 days.

(21) Appl. No.: 10/177,155

(22) Filed: Jun. 24, 2002

(65) Prior Publication Data
US 2003/0023269 A1    Jan. 30, 2003

Related U.S. Application Data

(63) Continuation of application No. 09/985,868, filed on Nov. 6, 2001, now abandoned, which is a continuation-in-part of application No. PCT/NL00/00295, filed on May 8, 2000.

(30) Foreign Application Priority Data
May 7, 1999    (NL) .................................. 1011997

(51) Int. Cl.
*A61N 1/00*    (2006.01)
(52) U.S. Cl. ......................................................... 607/2
(58) Field of Classification Search .................. 607/30, 607/2, 59, 13, 100–103; 128/904; 600/13, 600/585
See application file for complete search history.

(56) References Cited

U.S. PATENT DOCUMENTS

| | | | | |
|---|---|---|---|---|
| 4,305,402 A | * | 12/1981 | Katims | 600/554 |
| 4,919,139 A | * | 4/1990 | Brodard | 607/59 |
| 5,544,661 A | * | 8/1996 | Davis et al. | 600/513 |
| 5,634,939 A | | 6/1997 | Kuster et al. | 607/59 |
| 5,836,993 A | * | 11/1998 | Cole | 607/59 |
| 5,935,224 A | * | 8/1999 | Svancarek et al. | 710/63 |
| 6,024,699 A | * | 2/2000 | Surwit et al. | 600/300 |
| 6,162,460 A | * | 12/2000 | Lee | 424/449 |
| 6,301,506 B1 | * | 10/2001 | den Boer et al. | 607/100 |

(Continued)

FOREIGN PATENT DOCUMENTS

DE    36 05148    8/1987

(Continued)

OTHER PUBLICATIONS

International Search Report dated Aug. 30, 2000 from PCT/NL00/00295.

(Continued)

*Primary Examiner*—George Manuel
(74) *Attorney, Agent, or Firm*—Fish & Richardson P.C.

(57) ABSTRACT

An assembly for the purpose of self-treatment by electromagnetic waves. The assembly includes a transmitting coil arranged to transmit electromagnetic waves, the transmitting coil comprising a case in which an electromagnetic coil is accommodated. The coil is connected to a cord which, at the end remote from the case, is fitted with a plug suitable for connection to an output of a personal computer, or the like, associated with a patient. The computer or other component of the assembly also is provided with an access code for accessing a treatment site on the internet or other computer network. The treatment site is arranged for transmitting to the patient's computer a data file which, upon being processed therein, generates via the transmitting coil, a treatment signal tailored to the respective patient.

14 Claims, 1 Drawing Sheet

U.S. PATENT DOCUMENTS 6,312,376 B1 * 11/2001 Koren et al. .................. 600/13
6,491,647 B1 * 12/2002 Bridger et al. .............. 600/585

FOREIGN PATENT DOCUMENTS

| | | |
|---|---|---|
| DE | 40 18 063 A1 | 12/1991 |
| DE | 44 46 479 A1 | 6/1996 |
| GB | 2 073 593 A | 10/1981 |
| WO | WO 96/11723 | 4/1996 |

OTHER PUBLICATIONS

The International Preliminary Examination Report dated Aug. 1, 2001 for PCT/NL00/00295.

\* cited by examiner

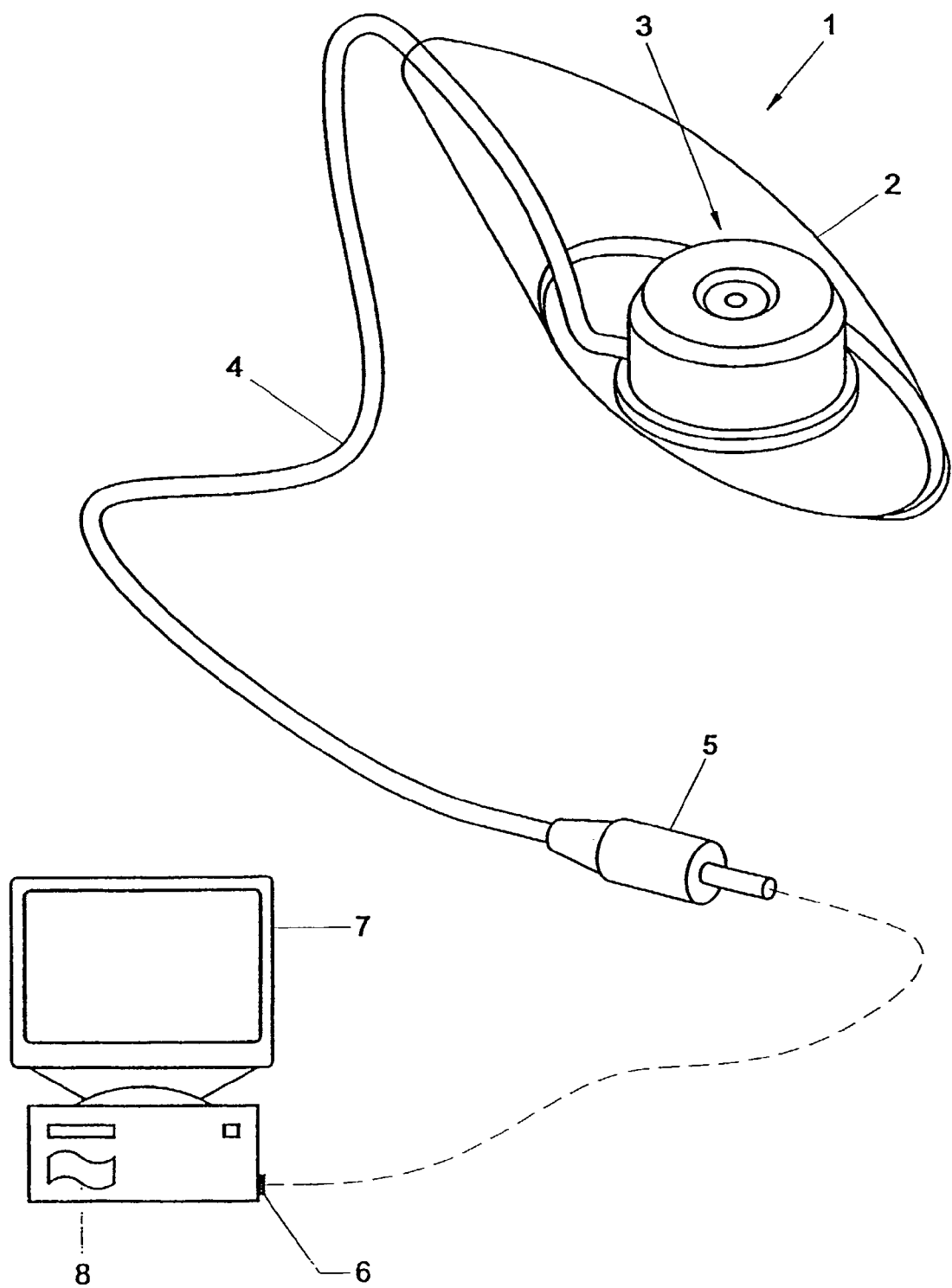

SELF TREATMENT DEVICE

RELATED APPLICATIONS

This is a Continuation of U.S. Application Ser. No. 09/985,868, filed Nov. 6, 2001, now abandoned, which is a Continuation of the U.S. National Stage Designation of PCT/NL00/00295, filed May 8, 2000, which published in English on 16 Nov. 2000.

FIELD OF THE INVENTION

This invention relates to an assembly for treating patients by means of electromagnetic waves.

BACKGROUND OF THE INVENTION

Such an assembly is described in U.S. Pat. No. 6,301,506. The assembly described therein is intended for determining a treatment frequency suited for a specific patient.

To that end, by means of a transmitting coil, the patient is subjected to a number of different frequencies, and the reaction of the body of the patient to these different frequencies is measured by means of sensors, such as, for instance, temperature sensors or skin resistance sensors. Next, on the basis of the variations measured by the sensors, a treatment frequency is determined by means of an algorithm. Thereafter, the patient can be treated a number of times using the treatment frequency as determined.

This treatment, which must take place, for instance, every week, is fairly simple, in the sense that a transmitting coil is to be held in the proximity of points of the body to be determined by the treating person, whereafter subsequently during a particular period, via the transmitting coil, electromagnetic waves are transmitted for influencing the patient's autonomic nervous system. In the assembly described, the transmitting coil is connected to a frequency generator which forms part of the assembly described. The assembly described includes a costly control, the purchase of which is justifiable only for treating therapists and not for the patient himself. It is therefore necessary that the patient, for the treatment to be carried out, periodically goes to the treating therapist to undergo the treatment there.

SUMMARY OF THE INVENTION

The present invention provides an assembly for the purpose of self-treatment by means of electromagnetic waves, the assembly comprising a transmitting coil arranged for transmitting electromagnetic waves, the transmitting coil comprising a case in which an electromagnetic coil is accommodated, the coil being connected to a cord which at the end remote from the case is fitted with a plug connectable to an output of a personal computer of a patient, the assembly further comprising an access code for access to a treatment site on the internet or like computer network, the site being arranged for transmitting via the network to the computer of the patient a data file which upon being processed in the computer of the patient generates via the transmitting coil connected to the computer a treatment signal tailored to the respective patient.

The patient, preferably after visiting a therapist or physician, can purchase an assembly according to the invention. By connecting the transmitting coil to his computer, and logging in on the treatment site through the access code, the patient can there retrieve a data file tailored to him.

Upon being processed in the patient's computer, this data file will generate on the respective output of the computer a signal that is suited for the treatment of the patient. In addition, the treatment site may also provide instructions about the position of the coil with respect to the body.

To that end, for instance, a representation of a patient may be displayed with an indication of the intended position of the transmitting coil.

The data file in question can be placed on the treatment site by the treating therapist or physician.

According to a further elaboration of the invention, however, it is also possible that the assembly comprises at least one sensor, such as, for instance, a temperature and/or skin resistance sensor, which is provided with an output suitable for connection to an input of a personal computer.

When the treatment site is provided with software for determining the treatment frequency suitable for a specific patient, it can be measured with the at least one sensor at what treatment frequency the optimum effect is obtained. For an accurate description of the determination of the treatment frequency, reference is made to NL-A-1009568. It is therefore actually possible to purchase the apparatus without visiting a treating therapist. The patient connects the sensor and logs on to the site by means of his access code. The site instructs him further about the steps to be taken, such as placing the sensor on the body. Next, the correct treatment frequency or frequencies is or are determined and the treatment can be started. The treatment site may also provide the patient with instructions about the times at which the treatment is to be repeated or continued.

Optionally, via the treatment site, the patient can fill in a questionnaire about the progress of the healing process, on the basis of which treatment may possibly be adjusted.

According to a further elaboration of the invention, the assembly is characterized in that via the transmitting coil the data file generates electromagnetic waves of a frequency in the range of about 30 to about 300 Hz, preferably in the range of about 100 to about 160 Hz. According to a still further elaboration, the generated electromagnetic waves may be of the harmonic, square or sawtooth type. The transmission power of the transmitting coil is preferably in the range of about 3 to about 20 milliwatt.

The plug of the transmitting coil which is suitable for connection to the computer output is preferably a jackplug, a mini jackplug, a DIN plug or a US plug.

BRIEF DESCRIPTION OF THE DRAWINGS

The present invention is described with reference to the attached drawing. The drawing shows an exemplary embodiment of an assembly for the purpose of self-treatment by means of electromagnetic waves.

DETAILED DESCRIPTION OF THE PREFERRED EMBODIMENT

To clarify the invention, it will be further elucidated on the basis of an exemplary embodiment, with reference to the drawing. The drawing shows an exemplary embodiment of an assembly for the purpose of self-treatment by means of electromagnetic waves. With these, inter alia the autonomic nervous system is influenced, which can be measured, for instance, on the basis of a change in skin resistance, local body temperature or like measurable body data. Also the meridian points according to traditional acupuncture are influenced, which is measurable with equipment known per se for measurement on the acupuncture points, for instance with the system PROGNOS.

The assembly comprises a transmitting coil 1 which is adapted for transmitting electromagnetic waves. The transmitting coil 1 comprises a case 2, shown in a transparent representation in the drawing, in which an electromagnetic coil 3 is accommodated. The coil 3 is connected to a cord 4 which at the end remote from the housing 2 is provided with a plug 5 which is suitable for connection to the output 6 of a computer 7. In the present exemplary embodiment, the plug 5 is a jackplug. It will be clear that other plugs suitable for connection to a computer output 6 can also be used, such as, for instance, a mini jackplug, a DIN plug or a USB plug. In the present exemplary embodiment, the coil 3 has a hollow core of 32 mm and comprises 200 turns of copper wire of a diameter of 0.3 mm. The transmission power of the coil is in the range of about 3 to about 20 milliwatt.

By means of an access code supplied along with the assembly, a data file 8 can be downloaded from a treatment site on a computer network, such as, for instance, internet. This data file 8 can be played directly, or after it has been stored on the hard disk of the computer 7 of the patient, so that via the transmitting coil 1 connected to the output 6, electromagnetic waves are transmitted which influence the patient's autonomic nervous system in the desired manner. Here, use is made of the treatment frequency determined by the therapist, which is stored in the data file. The treatment frequency can also be determined by an algorithm or program on the basis of body data such as temperature or skin resistance as sensed by sensors.

Sensors of a different type can also be employed. To be considered here are, for instance, sensors with which measurements on acupuncture points can be performed or sensors with which the blood composition or the composition of exhaled air can be measured directly. Preferably, the treatment frequency is in the range of about 30 to 300 Hz, more particularly in the range of about 100 to about 160 Hz. By means of the assembly according to the invention, the patient can carry out the treatment himself at home without this requiring a therapist. The therapist's only function is to determine the correct treatment frequency and to provide via the treatment site the data file 8 as well as instructions about the times at which the treatment is to be carried out and the positions with respect to the body where the transmitting coil is to be held. As already indicated hereinbefore, the patient may even determine the treatment frequency himself and compile a data file 8 without intervention of a therapist, when the apparatus is provided with sensors connectable to the computer, for measuring body data, such as temperature and/or skin resistance, and with a treatment frequency determination algorithm, which can be carried out by the personal computer. The algorithm may then be adapted for successively transmitting different frequencies via the transmitting coil 1 connected to the output 6, and for storing the response of the body to these different frequencies as measured by the sensors, whereupon the algorithm determines the treatment frequency as being the frequency at which the response of the body as measured by the sensors is strongest. On the basis of this measurement, the algorithm can subsequently create a suitable data file 8 which is suited to the specific patient.

It will be clear that the invention is not limited to the exemplary embodiment described, but that various modifications are possible within the framework of the invention. Thus the transmitting coil may be provided with a different number of turns, a different diameter or a different type of conducting wire. The shape of the case may also be different.

What is claimed is:

1. An electromagnetic wave self-treatment assembly comprising a transmitting coil (1) arranged for transmitting electromagnetic waves, the transmitting coil (1) comprising a case (2) in which an electromagnetic coil (3) is accommodated, the coil (3) being connected to a cord (4) which at the end remote from the case (2) is fitted with a plug (5) connectable to an output (6) of a personal computer (7) of a patient, the assembly further comprising at least one sensor for measuring at least one of a temperature or a skin resistance to provide a measured value, said sensor being provided with an output suitable for connection to an input of the computer (7), and the assembly further comprising an access code, tangibly embodied in a computer readable medium, for enabling remote access to a treatment site on a computer network, the treatment site being arranged for transmitting via the network to the computer (7) of the patient a data file (8) which upon being processed in the computer (7) of the patient generates, via the transmitting coil (1) connected to the computer (7), a treatment signal tailored to the respective patient, the treatment signal having a frequency that is determined by the computer (7) based upon the measured value.

2. The electromagnetic wave self-treatment assembly according to claim 1, wherein the plug (5) is a jackplug, a mini jackplug, a DIN plug or a USB plug.

3. The electromagnetic wave self-treatment assembly according to claim 1, wherein a transmission power of the transmitting coil (1) is in the range of about 3 to about 20 milliwatt.

4. The electromagnetic wave self-treatment assembly according to claim 1, wherein the computer network is the internet.

5. The electromagnetic wave self-treatment assembly according to claim 1, wherein the data file (8) causes generation of electromagnetic harmonic waves via the transmitting coil (1).

6. The electromagnetic wave self-treatment assembly according to claim 1, wherein the data file (8) causes generation of electromagnetic sawtooth waves via the transmitting coil (1).

7. The electromagnetic wave self-treatment assembly according to claim 1, wherein the data file (8) causes generation of electromagnetic square waves via the transmitting coil (1).

8. The electromagnetic wave self-treatment assembly according to claim 1, wherein the access code is unique to each patient.

9. The electromagnetic wave self-treatment assembly according to claim 1, wherein the access code is unique to each assembly.

10. The electromagnetic wave self-treatment assembly according to claim 1, wherein the measured value is received by the computer (7) from the at least one sensor.

11. The electromagnetic wave self-treatment assembly according to claim 1, wherein the measured value is stored in the data file (8).

12. An electromagnetic wave self-treatment assembly comprising:
   a transmitting coil including:
     a case;
     an electromagnetic coil accommodated by said case; and
     a cord having a first end connected to said case, and a second end fitted with a plug;

a personal computer having an output configured to receive the plug, the personal computer being provided with an access code, tangibly embodied in a computer readable medium, for transmission to a treatment site on a computer network; and at least one sensor for measuring at least one of a temperature or a skin resistance to provide a measured value, said sensor being connected to an input of said personal computer, wherein:

the personal computer is configured to receive a data file transmitted from the treatment site over the computer network based on the access code;

the personal computer is further configured to process the data file to thereby output a treatment signal to the transmitting coil to thereby deliver an electromagnetic treatment tailored to a patient associated with said personal computer, the electromagnetic treatment having a frequency that is determined by the personal computer based upon the measured value;

the computer network is the internet;

a transmission power of the transmitting coil is in the range of about 3 to about 20 milliwatt;

the data file causes generation of one at least one of electromagnetic harmonic waves, electromagnetic sawtooth waves, and electromagnetic square waves via the transmitting coil; and the access code is unique to each patient.

13. A method of facilitating self-administered electromagnetic wave therapy comprising the steps of:

transmitting, from a personal computer to an internet-accessible treatment site, an authorized access code associated with a treatment program for a particular patient;

receiving, by the personal computer from the internet-accessible treatment site, at least one data file in response to said authorized access code, wherein said data file comprises a measured value corresponding to a measurement of at least one of a temperature or a skin resistance by a sensor connected to an input of said personal computer;

processing, by said personal computer, said at least one data file to thereby output a treatment signal corresponding to a treatment frequency that is determined based upon the measured value;

receiving, by a transmitting coil comprising an electromagnetic coil, said treatment signal from the personal computer;

generating, by said electromagnetic coil, at least one electromagnetic wave at the treatment frequency suitable for therapeutic use, based on said treatment signal.

14. The method according to claim 13, comprising the step of transmitting an access code that is unique to said particular patient.

* * * * *